United States Patent [19]
Burzynski et al.

[11] Patent Number: 5,951,520
[45] Date of Patent: Sep. 14, 1999

[54] SELF-BLUNTING NEEDLE MEDICAL DEVICES AND METHODS OF MANUFACTURE THEREOF

[75] Inventors: Mark J. Burzynski, Southbury; Alexander K. Jones, Trumbull, both of Conn.; Richard S. Kearns, Seattle, Wash.; John M. Polidoro; Carl R. Sahi, both of Coventry, Conn.; Chad C. Smutney, Stafford Springs, Conn.

[73] Assignee: Bio-Plexus, Inc., Vernon, Conn.

[21] Appl. No.: 08/772,002

[22] Filed: Dec. 19, 1996

[51] Int. Cl.⁶ .................................................. A61M 5/178
[52] U.S. Cl. ............................................. 604/170; 604/161
[58] Field of Search ...................................... 604/110, 158, 604/161, 162, 164, 170

[56] References Cited

U.S. PATENT DOCUMENTS

| | | |
|---|---|---|
| 1,527,291 | 2/1925 | Zorraquin . |
| 3,491,756 | 1/1970 | Bentov . |
| 3,536,073 | 10/1970 | Farb ........................................ 604/162 |
| 3,809,081 | 5/1974 | Loveless . |
| 4,121,588 | 10/1978 | Geiger . |
| 4,233,975 | 11/1980 | Yerman . |
| 4,274,408 | 6/1981 | Nimrod . |
| 4,525,157 | 6/1985 | Vaillancourt . |
| 4,529,399 | 7/1985 | Groshong et al. . |
| 4,613,329 | 9/1986 | Bodicky ................................... 604/158 |
| 4,627,841 | 12/1986 | Dorr . |
| 4,675,005 | 6/1987 | DeLuccia . |
| 4,721,506 | 1/1988 | Teves . |
| 4,801,295 | 1/1989 | Spencer . |
| 4,808,169 | 2/1989 | Haber et al. . |
| 4,810,248 | 3/1989 | Masters et al. . |
| 4,828,547 | 5/1989 | Sahi et al. ............................... 604/110 |
| 4,834,718 | 5/1989 | McDonald . |
| 4,846,805 | 7/1989 | Sitar . |
| 4,869,717 | 9/1989 | Adair . |
| 4,880,410 | 11/1989 | Rossmark . |
| 5,009,642 | 4/1991 | Sahi ....................................... 604/110 |
| 5,030,208 | 7/1991 | Novacek et al. . |
| 5,098,389 | 3/1992 | Cappucci . |
| 5,098,402 | 3/1992 | Davis . |
| 5,139,485 | 8/1992 | Smith et al. . |
| 5,201,710 | 4/1993 | Caselli . |
| 5,312,345 | 5/1994 | Cole . |
| 5,334,159 | 8/1994 | Turkel ..................................... 604/158 |
| 5,376,075 | 12/1994 | Haughton et al. ........................ 604/158 |
| 5,423,760 | 6/1995 | Yoon .................................... 604/170 X |
| 5,433,711 | 7/1995 | Balaban et al. . |
| 5,460,611 | 10/1995 | Alexander . |
| 5,470,318 | 11/1995 | Griffith, III et al. . |
| 5,527,284 | 6/1996 | Ohnemus et al. . |
| 5,527,291 | 6/1996 | Zadini et al. ......................... 604/158 X |
| 5,562,611 | 10/1996 | Transue . |
| 5,562,629 | 10/1996 | Haughton et al. ........................ 604/158 |
| 5,569,202 | 10/1996 | Kovalic et al. . |
| 5,573,510 | 11/1996 | Isaacson .................................. 604/158 |

*Primary Examiner*—Wynn Wood Coggins
*Assistant Examiner*—Deborah Blyveis
*Attorney, Agent, or Firm*—Law Office of Victor E. Libert; Victor E. Libert; Frederick A. Spaeth

[57] ABSTRACT

A self-blunting needle medical device comprises a needle cannula (18) fixed to a hub (20) having a receiving structure therein such as ferrule (22) and a movable blunting member (14) movably received within the cannula (18). Ferrule (22) defines a sleeve bore (38) extending therethrough, within which both the cannula (18) and the movable member (14) can be received and which establishes a coaxial relationship between them. The ferrule (22) defines a first guide surface (40) for directing the blunting end (14a) of the movable member (14) into the central bore of the cannula (18) during assembly. A second guide surface (42) performs the function of guiding the proximal end (18b) of the cannula (18) into ferrule (22) for mounting therein. Typically, the cannula (18) has a tissue puncture tip (18a). When the movable member (14) is retracted into the cannula (18), the puncture tip (18a) is exposed for use, e.g., injection into tissue. The movable member (14) is then moved to an extended position in which blunting end (14a) projects beyond the puncture tip (18a), to render the device safe with regard to subsequent accidental needle sticks.

16 Claims, 5 Drawing Sheets

FIG. 7

SELF-BLUNTING NEEDLE MEDICAL DEVICES AND METHODS OF MANUFACTURE THEREOF

BACKGROUND OF THE INVENTION

1. Field of the Invention

The present invention relates to medical devices comprising self-blunting needles and to methods of manufacture of such self-blunting needle medical devices. More specifically, this invention is directed to improved medical devices of the type including a needle and blunting member which are movable relative to each other and to a method of manufacture thereof.

2. Related Art

For reasons which have received wide publicity, there is substantial demand for single-use venipuncture products which may be employed by health care workers with minimal risk of incurring an accidental needle-stick wound. A highly successful product of this nature is a self-blunting needle assembly sold under the registered trademark "PUNCTUR-GUARD" by Bio-Plexus, Inc. of Vernon, Connecticut. The "PUNCTUR-GUARD" needle assembly is manufactured in accordance with the teachings of U.S. Pat. No. 4,828,547, entitled "Self-Blunting Needle Assembly and Device Including the Same", issued on May 9, 1989 to Carl R. Sahi et al. This patent is hereby incorporated by reference herein. In the "PUNCTUR-GUARD" product, a rod or probe-like blunting member is disposed within the bore of a needle cannula having a (usually beveled) puncture tip suitable for puncturing tissue. To prevent accidental needle-stick wounds from occurring after use of the device, the blunting member, which is retracted behind the puncture tip when the needle is injected into tissue, can be extended beyond the puncture tip of the needle cannula to effectively blunt the puncture tip by extending beyond it, so as to eliminate or at least greatly reduce the risk of accidental needle-stick punctures.

During production of self-blunting venipuncture products such as the "PUNCTUR-GUARD" needle assembly discussed above, the blunting member must be inserted into the back of the needle cannula. This is a process step which requires high placement accuracy. This high placement accuracy has, in the past, been achieved through the use of an adjustable position blunting member inserter which is responsive to signals provided by an optical sensor system. This process requires that the needle cannula be mounted in a hub to form a front needle sub-assembly and then positioned over a light source. If alignment conditions were perfect, light from the source would enter the beveled tip of the front needle, pass through the length of the front needle, and exit the back of the front needle as a perfect, i.e., circular, beam of light. The optical system would detect the circular beam of light, compute its position and generate control signals which would direct the blunting member inserter to bring the blunting member cannula into alignment with the front needle cannula.

Since alignment conditions are never perfect, it is difficult to detect the circular beam of light which is commensurate with precise alignment, i.e., variations within the components allow the front needle cannula to be slightly tilted within the front needle sub-assembly. The projected light beam may thus be located in an infinite number of locations. The optical system must, accordingly, locate the unique light beam for each individual front needle cannula and hub and then direct the blunting member sub-assembly inserter to this unique position for proper placement. Further, while the combination of the optical system and inserter can locate the back of the front needle cannula very accurately and then move the inserter to a position commensurate with the location, it does not precisely locate the blunting member which, of course, must enter the back of the front needle cannula for successful insertion. Thus, slight variations in the blunting member sub-assembly itself or misalignment in the clamping of the blunting member sub-assembly by the inserter can cause a failure to accurately mate the blunting member sub-assembly with the front needle sub-assembly. In summary, the step of insertion of the blunting member cannula into the back of the front needle cannula is inefficient and time-consuming.

When the above-described self-blunting needle technology is employed in a fluid collection needle, the fluid to be collected is drawn through the blunting member cannula and into an evacuated tube. Leakage of air through the space inherently existing between the blunting member outer diameter and the front needle inner diameter, such air thereafter flowing through the blunting member cannula into the collection tube, will cause undesirable foaming in the collection tube. Accordingly, in order to be suitable for use in a blood collection system, a self-blunting needle assembly must pass an air seal test. The requisite seal between the blunting member and front needle must be achieved in a manner which does not significantly impede the above briefly discussed assembly process or impede relative movement between the blunting member cannula and the needle cannula.

Therefore, there remains a need in the art for methods and apparatus which facilitate the manufacture of medical devices employing self-blunting needle technology.

Additionally, there remains a need in the art for methods and apparatus for preserving the integrity of fluid transferred through medical devices employing self-blunting needle technology by providing an improved fluid flow seal between the various components of such medical devices.

SUMMARY OF THE INVENTION

The present invention overcomes the deficiencies of the prior art discussed above by providing novel and improved self-blunting needle medical devices and methods of manufacture thereof. Generally, medical devices in accordance with the invention include a guide member having a guide surface which leads an internal member (one of either a needle cannula or a blunting member) into registration with the bore of a fixed external cannula member (the other of either the needle cannula and the blunting member).

More specifically, the present invention provides a self-blunting needle cannula device comprising the following components. An external component comprises a cannula member having an outside diameter, a cannula distal end and a proximal end, and an external member hub on the cannula member and spaced from the cannula distal end, the cannula member further defining a through-bore having a through-bore inside diameter. An internal component comprises an elongate internal member having a member distal end, and an internal component hub on the internal member and spaced from the member distal end, the internal member being disposed within the through-bore of the cannula member of the external component. In this construction, the external component comprises one of (i) a needle component wherein the cannula member comprises a needle cannula having a puncture tip at the cannula distal end thereof, and (ii) a blunting component wherein the cannula member comprises a blunting member having a blunt tip at the cannula distal end thereof The internal component comprises the other of (i) and (ii). The needle component and the blunting component are movable relative to each other between a retracted blunting component position in which the blunt tip is positioned short of the puncture tip of the needle cannula to leave the puncture tip exposed, and an extended blunting component position in which the blunt tip extends beyond the puncture tip of the needle cannula to effectively blunt the puncture tip. A guide member is disposed at the proximal end of the cannula member and has a first entry aperture of greater diameter than the through-bore inside diameter and a first gate aperture of lesser diameter than the first entry aperture. The first gate aperture is axially aligned with the through-bore adjacent to the proximal end of the cannula member. The guide member defines a first guide surface that converges as sensed moving from the first entry aperture to the first gate aperture, to thereby guide insertion of the internal elongate member into the through-bore during assembly of the needle cannula device.

Another aspect of the present invention provides that the guide member has a first end at which the first guide surface is formed and an opposite, second end at which is formed a second guide surface having a second entry aperture of greater diameter than the outside diameter of the cannula member and a second gate aperture of lesser diameter than the second entry aperture. The guide member further comprises a sleeve bore extending between and axially aligned with the first and second gate apertures. The proximal end of the cannula member is mounted within the sleeve bore and the cannula member extends through the second gate aperture. The second guide surface converges as sensed moving from the second entry aperture to the second gate aperture, to thereby guide the proximal end of the cannula member into the sleeve bore during assembly of the device.

Other aspects of the invention provide one or more of the following features, alone or in non-mutually exclusive combinations: a sealant lubricant may be disposed between the internal member and the through-bore; the guide member may comprise a ferrule disposed about the proximal end of the cannula member; the ferrule may be located within the external member hub; the diameter of the first gate aperture may be less than the diameter of the sleeve bore to define a stop shoulder at the first gate aperture; the diameter of the first entry aperture may be at least from about 2 to 10 times greater than the diameter of the sleeve bore; the diameter of the second gate aperture may be substantially equal to the outside diameter of the cannula member and the diameter of the second gate aperture may be at least from about 2 to 10 times greater than that of the sleeve bore; the guide member may be integrally formed as part of the external member hub or the guide member may comprise a discrete ferrule which is mounted within the external member hub; the external component may comprise the needle component and the internal component, the blunting component, or the external component may comprise the blunting component and the internal component, the needle component; and the device may be in combination with an actuation member for moving at least one of the blunting component and the needle component relative to each other to change the blunting component from its retracted position to its extended position.

Another aspect of the invention provides for the guide member to comprise a radially expanded extension of the proximal end of the cannula member.

In accordance with a method aspect of the present invention, there is provided a method for assembling a self-blunting needle cannula device, comprised of (i) an external component comprising a cannula member having an outside diameter, a cannula distal end, a proximal end and a through-bore having a bore inside diameter; and (ii) an internal component comprising an elongate internal member having an outside diameter and a member distal end. After assembly, the member distal end is disposed within the through-bore of the cannula member of the external component The method comprises the following steps. (a) There is interposed between the external component and the internal component a guide member having a first end and an opposite, second end, the guide member having at its first end a first entry aperture of greater diameter than the outside diameter of the first internal member, and a first gate aperture of lesser diameter than the first entry aperture and open to the second end of the guide member. The guide member defines a first guide surface that converges as sensed moving from the first entry aperture to the first gate aperture. (b) The internal component is positioned at the first end of the guide member with the distal end of the internal member facing and in register with the first entry aperture. (c) The external component is positioned at the second end of the guide member with the cannula distal end in coaxial alignment with the first gate aperture. (d) The internal component and the first guide surface are advanced towards each other so that the distal end of the internal member enters the first entry aperture and contacts the first guide surface, and the advancing is continued whereby the first guide surface guides the internal member through the first entry gate thence into the through-bore of the cannula member.

In accordance with another method aspect of the present invention, there is formed at the second end of the guide member a second entry aperture of greater diameter than the outside diameter of the cannula member, a second gate aperture of lesser diameter than the second entry aperture, and a second guide surface which converges as sensed moving from the second entry aperture to the second gate aperture, the guide member further comprising a sleeve bore extending between and coaxially aligned with the first and second gate apertures. With this structure, the positioning of step (c) further comprises disposing the cannula member with its proximal end in register with the second guide surface and advancing the cannula member and the second guide surface towards each other so that the proximal end of the cannula member enters the second entry aperture and contacts the second guide surface. The advancing is continued so that the second guide surface guides the proximal end of the cannula member into the sleeve bore and seats the proximal end of the cannula member therein.

Another method aspect of the invention provides for positioning the proximal end of the cannula member within the sleeve bore immediately adjacent to the first entry gate.

Yet another method aspect of the invention includes leaving the cannula member of the external component mounted within the guide member and utilizing the guide member as a component of the self-blunting needle cannula device.

In one method aspect of the invention, the external component comprises the needle component and the internal component comprises the blunting component; in another method aspect, the external component comprises the blunting component and the internal component comprises the needle component.

Yet another method aspect of the present invention further comprises installing the self-blunting needle assembly as described above in a medical fluid handling device comprising an actuation member for moving at least one of the blunting component and the needle component relative to each other to change the blunting component from its retracted position to its extended position.

Other aspects of the present invention are described below.

BRIEF DESCRIPTION OF THE DRAWINGS

In the accompanying drawings, like reference numerals refer to like elements in the several Figures.

FIG. 1A-1 is an end view taken along line X—X of FIG. 1;

FIG. 1B is an end view, taken along line B—B of FIG. 1A, but reduced in size relative to FIG. 1A;

FIG. 1C is a view similar to FIG. 1B of another embodiment of the ferrule;

DETAILED DESCRIPTION OF THE INVENTION AND PREFERRED EMBODIMENTS THEREOF

The present invention relates to self-blunting needle assemblies of the type that comprise a needle cannula and a blunting member. The blunting member may be disposed within the needle cannula but, in alternative embodiments, the blunting member may be hollow and the needle cannula may be disposed within the blunting member. In either case, the blunting member is movable relative to the needle cannula from a retracted position to an extended position. In the retracted position of the blunting member (which may also be considered an extended position of the needle cannula), the puncture tip of the needle cannula extends beyond the tip of the blunting member so that the puncture tip is unimpeded upon being inserted into tissue. When the blunting member is in the extended position (which may also be considered a retracted position of the needle cannula), the blunting member extends beyond the puncture tip of the needle cannula and thus effectively blunts it, thereby preventing, or at least severely inhibiting, the puncture tip from entering tissue. The present invention provides an improvement to such assemblies that simplifies the insertion of one of the needle cannula and the blunting member into the other and, accordingly, provides a simplified assembly procedure. The present invention provides a guide member having a guide surface formed about the central bore of the external one of the needle cannula and the blunting member, the guide surface being of greater diameter than the central bore of the external component (needle cannula or blunting member). Accordingly, when the internal member is to be inserted into the external member, it is no longer necessary to precisely align the internal member with the bore of the external member. Rather, the present invention allows for a mere approximate alignment of the two members because the internal member need only be aligned with the guide surface. The internal member is then advanced towards the bore of the external member and, if the two are not precisely aligned, the guide surface, which is funnel-like in configuration, guides the end of the internal member into the external member. The guide surface may be defined by a surface of a guide member comprising a hub secured onto the end of the external member, or by a separate ferrule disposed at the end of the external cannula.

Figure 1:
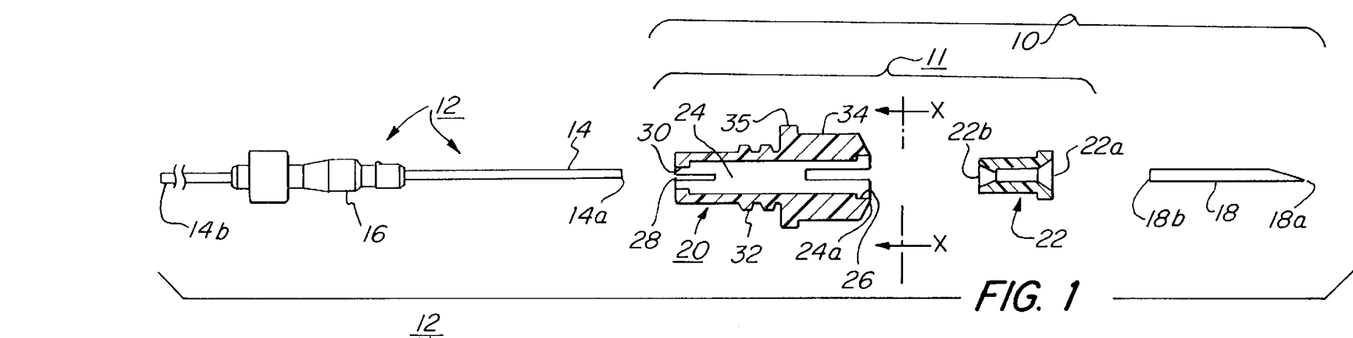
FIG. 1 is an exploded elevation view, partly in cross section, of a self-blunting needle device in accordance with one embodiment of the present invention in which the blunting member is disposed within the needle cannula.
Figure 2:
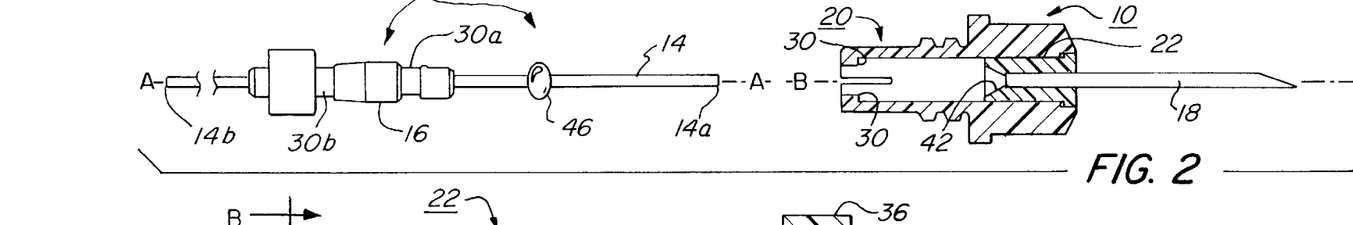
FIG. 2 is a view similar to that of FIG. 1 but showing the device in an assembled state with the body and viscous lubricant applied to the blunting member cannula.
Figure 2A:
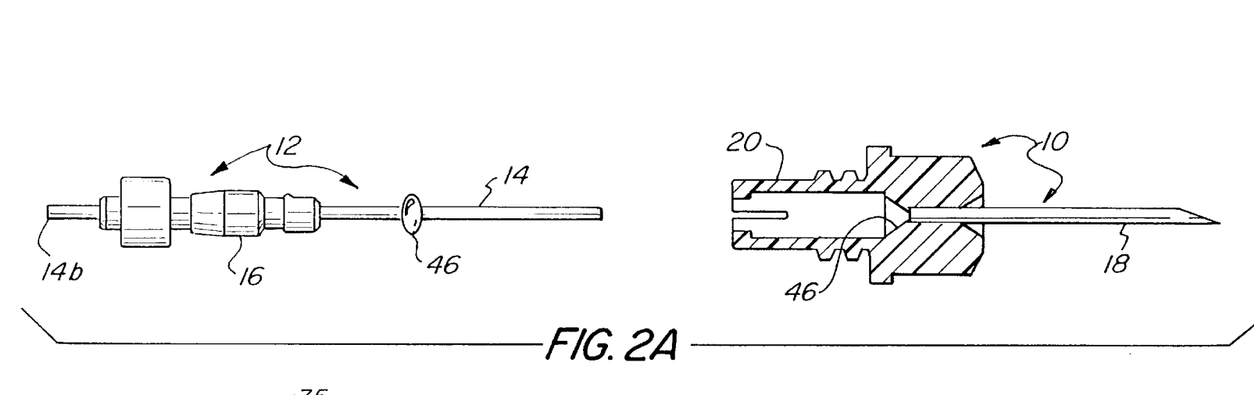
FIG. 2A is a view similar to that of FIG. 2 of an alternative embodiment of the invention.

With reference to FIGS. 1 and 2, a self-blunting needle cannula device in accordance with one embodiment of the present invention comprises an external component indicated generally at 10, and including a hub-ferrule sub-assembly 11, and an internal component indicated generally at 12. The external component 10 is depicted in an exploded state and is seen to comprise a cannula member in the form of a needle cannula 18, an external member hub 20 and a ferrule 22. As will be clear by reference to FIG. 2, hub 20 is mounted on cannula 18 by means of the ferrule 22. Needle cannula 18 has a distal end that comprises a puncture tip 18a for penetrating biological tissue, sealing membranes for specimen containers and the like, and an opposite, proximal end 18b that may be blunt. Needle cannula 18 has a central bore extending therethrough from the puncture tip 18a to the proximal end 18b, to permit the passage of fluid therethrough and, as explained below, to movably accommodate the blunting member of the internal member 12 therein. Hub 20 is preferably a generally tubular member, i.e., has a longitudinal hub bore 24 extending therethrough. Hub bore 24 is enlarged at the end of the hub from which needle cannula 18 extends to define a shoulder 26. Hub 20 is split at its end opposite from shoulder 26 so as to impart a degree of flexibility to that end. This split in hub 20 is formed by a pair of opposed slots 28. A pair of detents 30, which project into bore 24, are provided in the split end of hub 20. The detents 30, cooperate, in the manner shown in FIGS. 3 and 4, with recesses provided on the exterior of the internal component hub 16 of internal component 12 to hold blunting member 14 in particular positions relative to needle cannula 18, as further described below. In this illustrated embodiment, hub 20 is provided with an exterior thread 32 whereby the external component 10 may be engaged with a threaded needle holder of a fluid handling device such as a syringe (not shown). The hub 20 is also provided with a plurality of external fins 34, oriented generally radially with respect to the axis of bore 24, which external fins extend from a circumferential flange 35 at the end of thread 32 to the end of hub 20 where the shoulder 26 is located. The external fins 34 facilitate handling of the hub 20 to install or remove external component 10 into or out of a holder or other device (not shown).

Figure 1A:
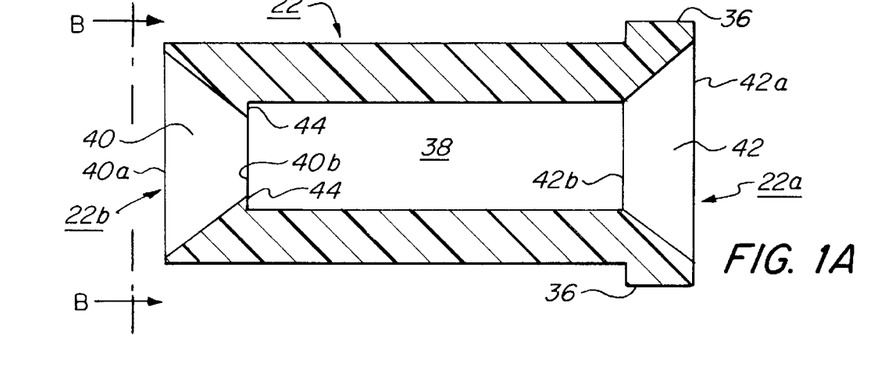
FIG. 1A is an enlarged view of the ferrule 22 of FIG. 1.
Figures 1A, 1B, 1C:
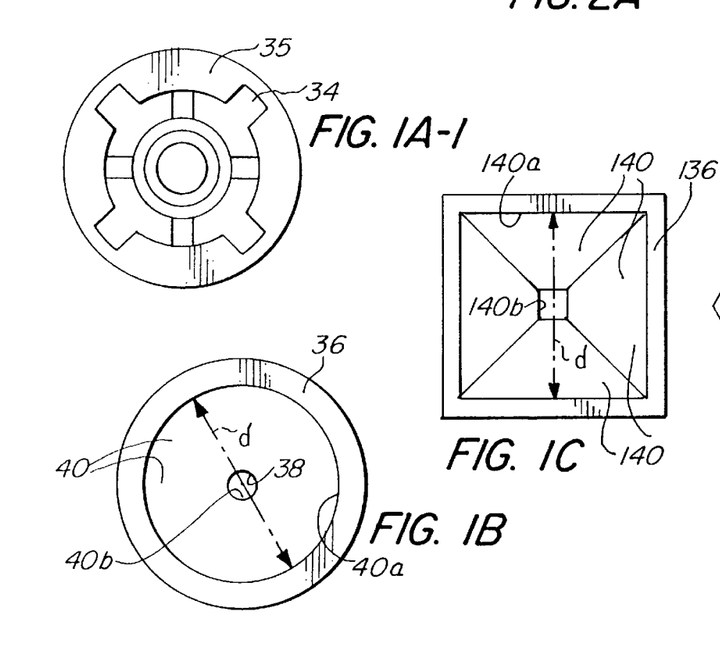

As best shown in FIG. 1A, the ferrule 22 has a first end 22a and a second end 22b and is sized and shaped to be inserted, as a press fit, into the first end 24a of hub bore 24 of hub 20. Referring to FIGS. 1A and 1B, ferrule 22 has a circumferential ferrule flange 36, which is complementary in shape to the recess which defines shoulder 26 (FIG. 1) of external member hub 20. Ferrule 22 may optionally be glued in place within hub 20. Ferrule 22 is a substantially tubular member, and is provided with a sleeve bore 38 that diverges at the two opposite ends thereof where the ferrule 22 defines conical lead-ins, i.e., a first guide surface 40 and a second guide surface 42. Guide surface 40 defines a first entry aperture 40a at the mouth of the sleeve bore 38, and a first gate aperture 40b disposed at the first end of sleeve bore 38. First entry aperture 40a is of significantly larger diameter, preferably at least about 2 to 10 times as large, as the diameter of first gate aperture 40b. The first entry aperture need only be large enough to readily permit insertion therein of a cannula or rod-like member during assembly of the self-blunting needle cannula device without need to resort to optical alignment equipment or other extraordinary measures. Needle cannula stock used in medical devices typically ranges in outside diameter from about 0.203 inches (gage 6RW) to about 0.006 inches (gage 34RW). A useful range of diameter for first entry aperture 40a (and for second entry aperture 42a) described below, is from about 0.030 to 0.300 inches. The diameter of first gate aperture 40b preferably is the same as or slightly smaller than the inside diameter of the cannula of external component 10.

Figure 1D:
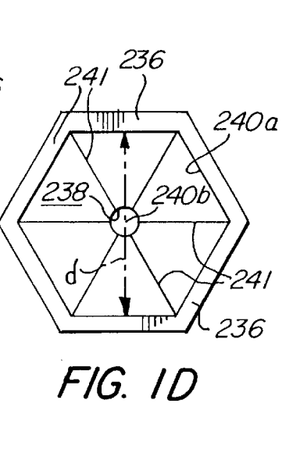
FIG. 1D is a view similar to FIG. 1B, but of a third embodiment of the ferrule.
Figure 1E:
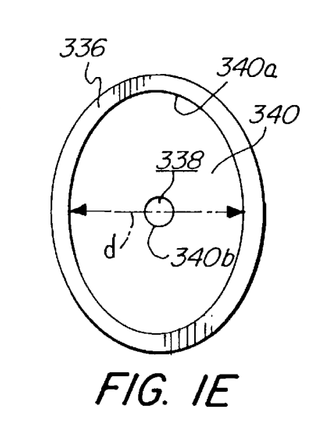
FIG. 1E is a view similar to FIG. 1B, but of a fourth embodiment of the ferrule.

Reference to the diameters of the entry apertures 40a, 42a, and the gate apertures 40b, 42b, and the truncated right-angle conical construction of first guide surface 40 and second guide surface 42, should not be taken to mean such circular/conical construction is essential to the present invention. For example, FIG. 1C, 1D and 1E illustrate alternate embodiments of non-circular construction of first entry and gate apertures and non-conical construction of the first guide surface. FIG. 1C shows a first guide surface 140 comprised of four trapezoidal-shaped flat surfaces extending between a first entry aperture 140a and a first gate aperture 140b, both apertures being square in cross-section in the illustrated embodiment. First gate aperture 140b leads to sleeve bore 138. Obviously, a rectangular configuration other than a square may be used, e.g., any suitable polygonal configuration may be used. The circumferential ferrule flange 136 of the FIG. 1C embodiment is also shown as square in cross-sectional view but, alternatively, circumferential ferrule flange 136 could be circular in cross-section, with the remainder of the construction being as shown in FIG. 1C.

FIG. 1D illustrates another embodiment in which first entry aperture 240a and circumferential ferrule flange 236 are of hexagonal configuration, and first gate aperture 240b is of circular configuration. In this embodiment, the trapezoidal-shaped surfaces connecting the hexagonal first entry aperture 240a to first gate aperture 240b may be flat, or they may be curved surfaces defining valleys which meet at crests which lie along the lines 241. First gate aperture 240b leads to sleeve bore 238.

FIG. 1E shows yet another embodiment of which the first entry aperture 340a is oval in cross-sectional view, and the first gate aperture 340b is circular. The latter leads to sleeve bore 338. In this case the first guide surface 340 is a smooth, curved surface and circumferential ferrule flange 336 is of oval configuration in cross sectional view.

Obviously, other variations of the construction of the first (and second) guide surface may be utilized, such as polygonal configurations other than a square, rectangle or hexagon, and even irregularly shaped entry and gate apertures may be used if necessary to accommodate a particular construction. Equally obviously, the same applies to the second entry and gate apertures and the second guide surface. In all cases, reference herein and in the claims to the "diameter" of the entry and guide surfaces refers to the smallest diameter thereof as illustrated in each of FIGS. 1B through 1E by the diameter lines d.

Returning now to the description of the ferrule 22, first gate aperture 40b thereof is slightly smaller in diameter than sleeve bore 38 and, accordingly, provides an annular stop shoulder 44 at the junction of first guide surface 40 and the adjacent portion (first end) of sleeve bore 38. At the opposite end of ferrule 22, second guide surface 42 extends between a second entry aperture 42a and a second gate aperture 42b. The first gate aperture 40b is slightly smaller in diameter than the second gate aperture 42b, which is the same diameter as sleeve bore 38.

External component 10 is assembled by inserting the second end 22b of ferrule 22 into the first end 24a of the bore 24 in hub 20 until ferrule flange 36 engages shoulder 26. Then, the proximal end 18b of needle cannula 18 is inserted through second entry aperture 42a via second guide surface 42 and second gate aperture 42b into sleeve bore 38 of ferrule 22 until proximal end 18b seats against stop shoulder 44, thus producing an assembled external component 10 as shown in FIG. 2. The outer diameter of needle cannula 18 is about the same as, or only very slightly less than, the diameter of sleeve bore 38. The insertion of the proximal end 18b into ferrule 22 is facilitated by the guiding action of the second guide surface 42, second entry aperture 42a providing a larger "target" for insertion of needle cannula 18b and the truncated conical shape of second guide surface 42 guiding proximal end 18b into sleeve bore 38. Optionally, needle cannula 18 and ferrule 22 may be glued in place, e.g., by an ultraviolet ("UV")-curable adhesive, as is known in the art.

The internal component 12 is assembled in a similar, conventional manner, e.g., by inserting the blunting member 14 through the internal component hub 16 and securing the hub 16 in place thereon, e.g., by the use of a UV-curable adhesive. The first end of blunting member 14 is provided by a blunt end 14a which, under ordinary hand pressure, will not easily puncture human skin or other biological tissue. The opposite end 14b of blunting member 14 extends beyond internal component hub 16, in the direction facing opposite to blunt end 14a.

To prepare for the assembly of a self-blunting cannula device, internal component 12 is disposed so that the longitudinal axis A—A (FIG. 2) of internal component 12 is in approximately parallel relation to the longitudinal axis B—B (FIG. 2) of external component 10, with the blunt end 14a of blunting member 14 in register with first guide surface 40 of ferrule 22. Then, internal component 12 is advanced towards external component 10 until the first end 14a of blunting member 14 passes through first entry aperture 40a and contacts first guide surface 40 which, with continued advancement of internal component 12, guides the blunt end 14a of blunting member 14 through first gate aperture 14b thence into the bore of needle cannula 18. As with the insertion of proximal end 18b of cannula needle 18 into ferrule 22, the first entry aperture 40a provides a longer target than sleeve bore 38 and the bore of needle cannula 18, and the truncated conical shape of first guide surface 40 guides blunting member 14 into place. Thus, the self-blunting cannula assembly can be disposed in the ready-to-use configuration illustrated in FIG. 3. It is thus readily seen that, by providing a first guide surface 40, it is not necessary to precisely align the internal component 12 with the bore of the external component needle cannula 18, as was necessary with the prior art, and the formerly required elaborate optical positioning, or other such equipment, may be dispensed with.

Preferably, the first gate aperture 40b is not larger in diameter than the sleeve bore 38 at least at the first end thereof, so that the formation of a lip or shoulder facing first entry aperture 40a is precluded, as such lip or shoulder could inhibit entry of the blunting member 14 therein. Optionally, first guide surface 40 may be formed as an integral part of hub 20, as indicated in FIG. 1A. In any case, by providing a first guide surface 40 that preferably defines a first gate aperture 40b that is no larger than the interior of needle cannula 18, the insertion of internal component 12 into external component 10 is simplified. Generally, first guide surface 40 (like second guide surface 42) preferably is shaped like a truncated right-angle cone.

The internal component 12 and the external component 10 can be prepared separately and, optionally, simultaneously. In such production, where adhesive bonding is employed, a UV-curable adhesive will optimally be utilized. The internal component 12 may be fabricated by dropping the blunting member 14 into the internal component hub 16 and adhesively bonding the parts. The external component 10 may be fabricated by first pressing the ferrule 22 into the hub 20. Then, the proximal end 18b of needle cannula 18 is guided, by means of the second guide surface 42, into ferrule 22 until end 18b seats upon shoulder 44. Second guide surface 42 extends between second entry aperture 42a and second gate aperture 42b and is, like first guide surface 40, shaped like a segment of a right-angle cone. Optionally, needle cannula 18 may be gravity-fed into ferrule 22. When needle cannula 18 is in place in ferrule 22, it may be adhesively secured therein.

To complete the assembly, the internal component 12 is disposed with its longitudinal axis A—A generally parallel to the longitudinal axis B—B of the external component 10, with the first end of the internal component 12 in register with the first entry aperture 40a of first guide surface 40, to facilitate insertion of the internal component 12 into the external component 10. Reference to the end of the internal component 12 being in-"register" with the first entry aperture 40a means that when the internal component 12 and the external component 10 are brought together in a direction substantially parallel with their respective longitudinal axes, the end of the blunting member 14 will pass through first entry aperture 40a to contact the first guide surface 40. When the internal component 12 is so disposed, it is advanced towards the first gate aperture 40b of first guide surface 40. Ultimately, the blunt end 14a of the internal component 12 contacts the first guide surface 40a and, as the internal component is advanced further, the funnel-like or conical configuration of first guide surface 40 will lead the end of blunting member 14 to the first gate aperture 40b at the end 18b of the bore of needle cannula 18. Since the first gate aperture 40b is no larger than the interior bore of needle cannula 18, first guide surface 40 will readily guide blunting member 14 into the central bore of needle cannula 18 without "hanging up" or catching at first gate aperture 40b. (It will be understood that the advancing motion is a relative term and that this phrase applies equally to procedures in which the internal component is held stationary while the external cannula component is moved "backward" towards it, or both are moved towards each other.) In the illustrated embodiment, the completed self-blunting needle assembly 15 (FIG. 3) is ready for use when the blunting member 14 is held in the retracted position shown in FIG. 3, as described more fully below.

Figure 3:
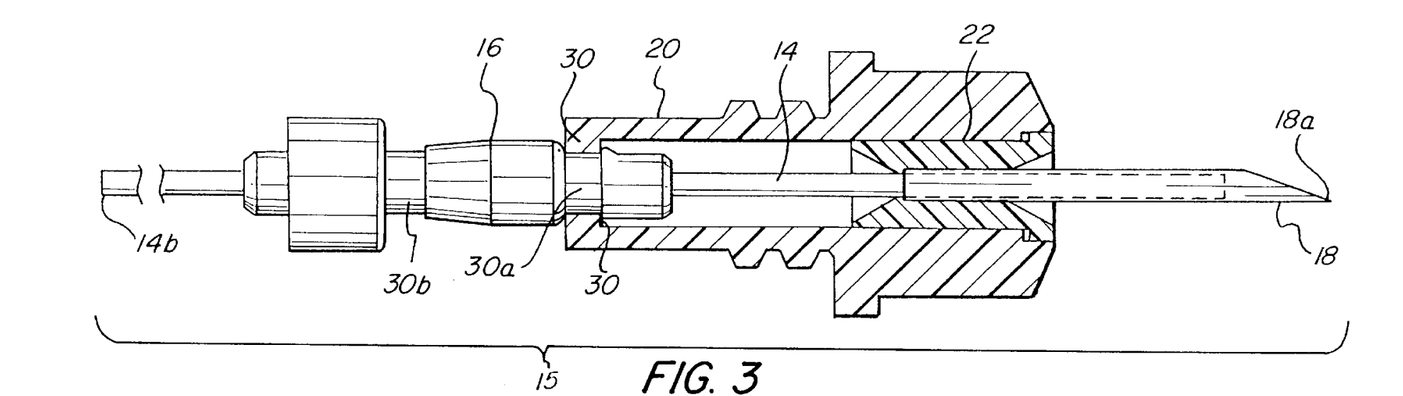
FIG. 3 is an elevation view, partly in cross section, of the needle device of FIGS. 1 and 2 in the ready-to-use condition showing the blunting member in the retracted position.

Preferably, the external diameter of blunting member 14 is a close fit with the internal diameter of needle cannula 18 so that the puncture tip 18a lies flat on the surface of the blunting member when the blunting member is in its extended position, shown in FIG. 3. To allow fluid flow through the cannula, it is therefore necessary in this preferred embodiment that the blunting member be hollow and that it have a central bore extending therethrough. In alternative embodiments, however, an internal blunting member need not be hollow to accommodate fluid flow therethrough, but in such case the blunting member must have a diameter sufficiently smaller than the internal diameter of the needle cannula to allow adequate fluid flow in the annular space between them.

When the internal component is dimensioned and configured for a close fit with the interior bore of the external component, it may be desirable to lubricate their mating surfaces and to provide a seal between them to prevent the unwanted flow of air bubbles. Accordingly, in the illustrated embodiment of FIGS. 1–3, a drop of viscous sealant-lubricant, indicated at 46 in FIG. 2, is applied to the blunting member 14. Because of its viscosity, the lubricant will assume the shape of an annulus, i.e., the lubricant will extend completely about the blunting member cannula 14. In the practice of the present invention, satisfactory results have been achieved by employing a thickened lubricant having a viscosity which is comparable to that of petroleum jelly, such as a thickened lubricant available from NuSil Technologies Company of Carpenteria, Calif. After the viscous lubricant 46 has been applied, the internal component 12 is advanced into hub 20. This relative motion will result in the projecting detents 30 at the split end of hub 20 snapping into the first annular groove 30a formed in the exterior of the internal component hub 16 of the internal component 12. At this juncture, the self-blunting needle assembly 15 will be in the state depicted in FIG. 3, in which the self-blunting needle assembly 15 is ready to be incorporated into a medical device such as a syringe. At this time, the viscous lubricant 46 will be located in the annulus between the outer diameter of the blunting member 14 and the inner diameter of the needle cannula 18. The viscosity of the lubricant 46 ensures that a good seal will be established between the tubular blunting member 14 and needle cannula 18, thus ensuring that air cannot flow between the blunting member 14 and needle cannula 18 in response to the coupling of an evacuated tube to the opposite end 14b of the blunting member 14, i.e., the end of the blunting member disposed oppositely with respect to the end located within the needle cannula 18. The viscous lubricant also ensures that all fluid directed to such an evacuated tube or the like will flow through the tubular blunting member 14.

Figure 4:
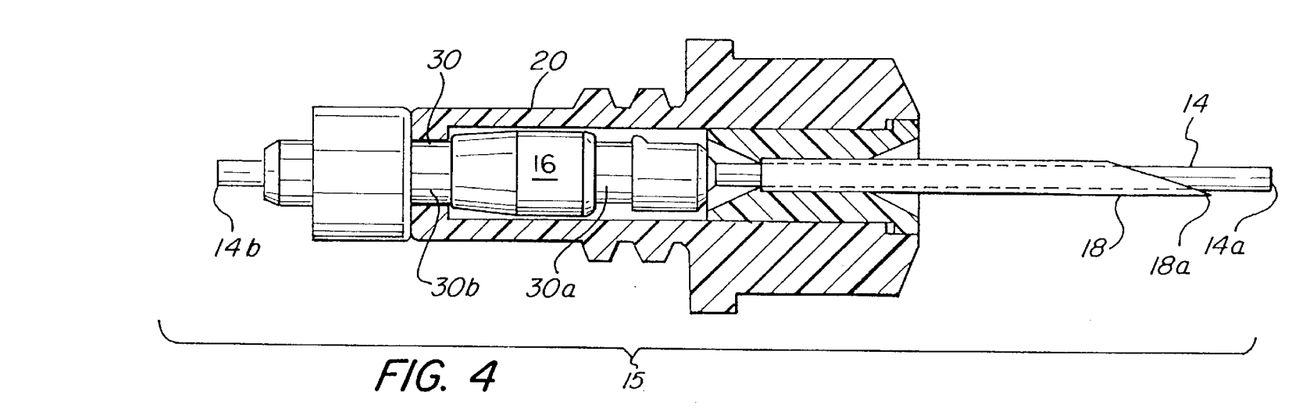
FIG. 4 is a view, similar to that of FIG. 3, showing the blunting member in the extended position.

As indicated above, internal component 12 is movable relative to external component 10 between an initial or retracted position as shown in FIG. 3, wherein the end of blunting member 14 is disposed within the front needle cannula leaving the puncture tip 18a exposed, and the extended position of FIG. 4 where the blunt first end 14a of blunting member 14 projects beyond the beveled puncture tip 18a, thus shielding puncture tip 18a in the sense that the blunt end prevents puncture tip 18a from effectively contacting tissue to penetrate the same. In a preferred embodiment, the internal component hub 16 and the external member hub 20 are mutually dimensioned and configured to provide an indexing function to set useful mutual positions of the internal component 12 within the external component 10. Two such indexed positions between the (blunting member) internal component 12 and the (needle) external component 10 are defined, in the illustrated embodiment, by annular grooves 30a, 30b provided on the exterior of internal component hub 16 (FIG. 2) and detents 30 of external member hub 20. Groove 30a is seated against detents 30 when the internal component 12 is in its retracted position shown in FIG. 3 and groove 30b is seated against detents 30 when internal component 12 is in its extended position shown in FIG. 4.

Figure 5:
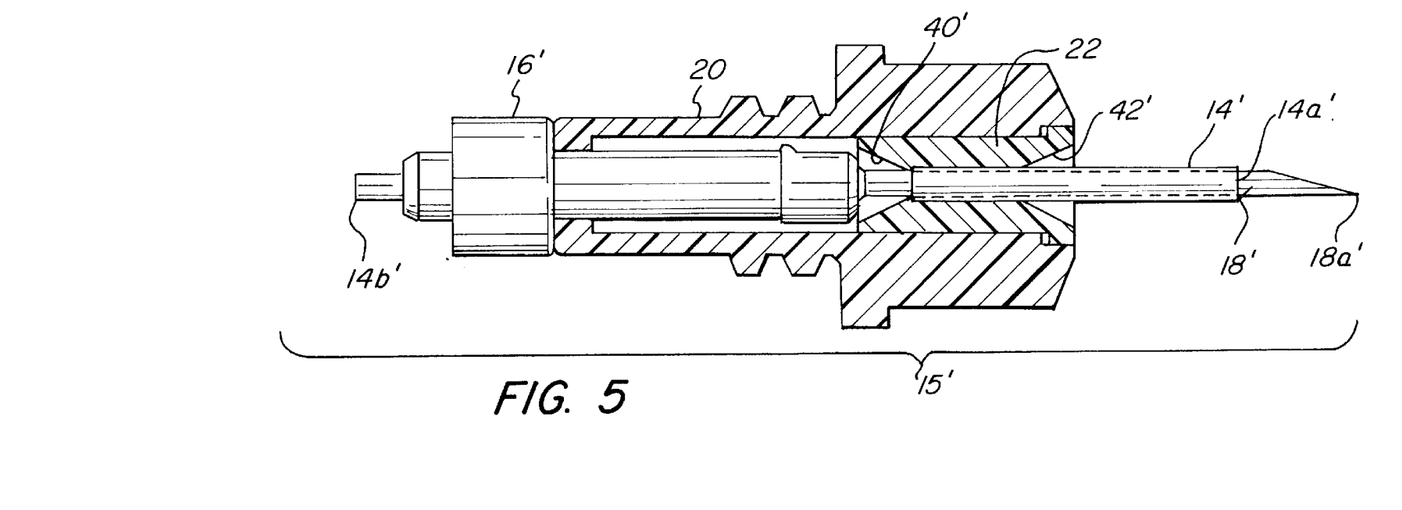
FIG. 5 is a side elevation view, partly in cross section, of a needle assembly in which the cannula is disposed within the blunting member in accordance with an alternative embodiment of the invention, showing the blunting member in the retracted position.
Figure 6:
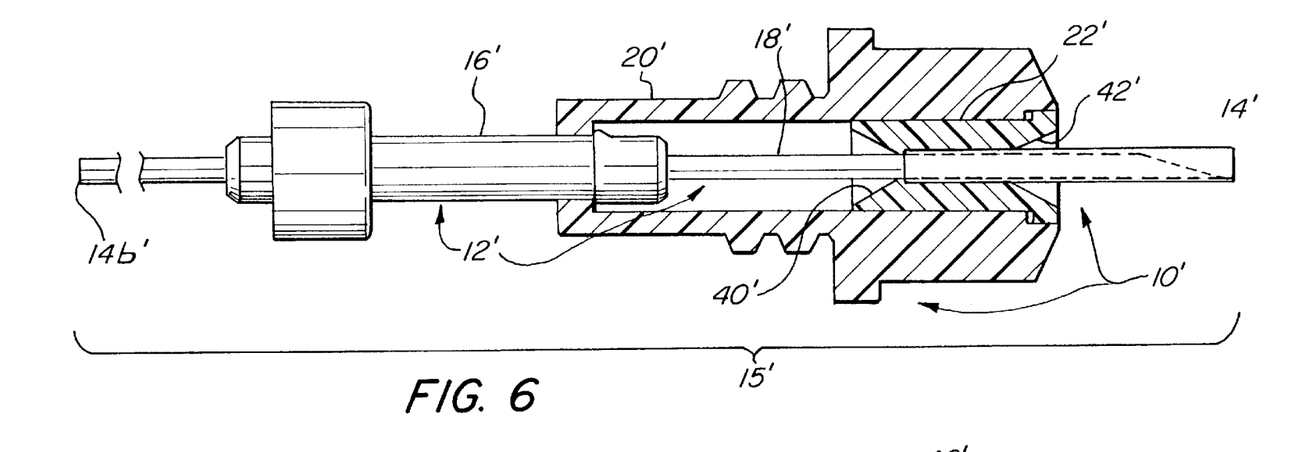
FIG. 6 is a view, similar to FIG. 5, showing the blunting member in an extended position.

With reference now to FIGS. 5 and 6, a self-blunting needle assembly 15' in accordance with an alternate embodiment of the present invention is shown. It should be appreciated that this alternate embodiment is similar to the embodiment of FIGS. 1–4 in both form and function and, therefore, like reference numerals have been used to refer to like elements, sometimes with a prime indicator. The primary difference between the embodiment of FIGS. 1–4 and the embodiment of FIGS. 5 and 6 is a reversal of the concentric relation between the blunting member and the needle cannula. That is, in the embodiment of FIGS. 5 and 6, the internal component 12' of the device comprises a needle cannula 18' and an internal component hub 16' thereon. The internal component 12' is disposed within an external component 10', i.e., within hollow blunting member 14' thereof. External component 10' further comprises the external member hub 20' within which blunting member 14' is fixedly mounted by means of a ferrule 22' associated therewith.

The self-blunting needle assembly 15' of FIGS. 5 and 6 is assembled in a manner which is substantially similar to that described with respect to the embodiment of FIGS. 1–4. That is, blunting member 14' is mounted in ferrule 22' in the same manner as described above for the mounting of needle cannula 18' into ferrule 20 of the FIGS. 1–4 embodiment, utilizing second guide surface 42'. Needle cannula 18' is then inserted into hub 20 and is guided by first guide surface 40 to the interior bore of blunting member 14'. A lubricant is applied to the exterior of needle cannula 18' which is advanced until it projects beyond the blunt first end 14a' of blunting member 14', thus disposing blunting member 14' in a retracted position and exposing puncture tip 18a'. Upon use of needle assembly 15', blunting member 14' is moved into its extended position as seen in FIG. 6 to project beyond and thereby effectively blunt puncture tip 18a' and thus prevent subsequent needle sticks. Stated conversely, after use, needle cannula 18' is withdrawn into a retracted position within blunting member 14' to effectively blunt puncture tip 18a'. It will be noted that the embodiment of FIGS. 5 and 6 lacks the equivalent of grooves 30a, 30b shown in the embodiment illustrated in FIGS. 2–4. In the embodiment of FIGS. 5 and 6, other means (not shown) may be employed to retain the components in the respective positions illustrated in FIGS. 5 and 6. For example, locking or detent means may be provided on an actuator which engages opposite end 14b' in order to retain internal component 12' in its two positions illustrated in FIGS. 5 and 6. Alternatively, internal component hub 16' of FIGS. 5 and 6 could be configured to have grooves similar or identical to grooves 30a and b of the embodiment of FIGS. 2–4.

Naturally, the other component configurations and cooperation discussed above with respect to the first disclosed embodiment apply equally to the embodiment of FIGS. 5 and 6. Further, it should be noted that while needle cannula 18' could assume a variety of tubular configurations, needle 18' is preferably a hollow cannula sharpened at its puncture tip end. Such a configuration allows fluid to be transferred to and/or from a patient through needle 18' in an unobstructed manner.

Figure 7:
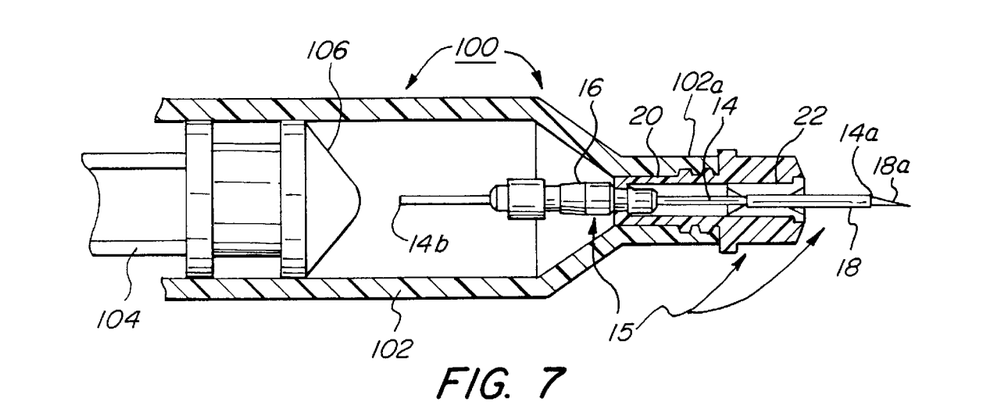
FIG. 7 is a schematic cross-sectional view of a syringe that incorporates a self-blunting needle assembly in accordance with one embodiment of the invention.

Self-blunting needle technology of the type to which the present invention relates may be employed in a wide variety of venipuncture products such as fluid-collection needles, syringes, catheters, infusion winged sets and various other medical sharps. To give but one particular example, FIG. 7 schematically illustrates a hypodermic syringe 100 that incorporates the self-blunting needle assembly 15 of FIGS. 3 and 4. Syringe 100 comprises a syringe body 102 which is configured to contain a conveniently sized aliquot of injection fluid for hypodermic delivery, e.g., body 102 may comprise a graduated 10 cc cylinder. An actuation member is provided by a plunger 104 on which is mounted a plunger head 106, which slides within body 102 while maintaining a liquid-tight seal therewith. Plunger 104 projects from the end (not shown) of body 102 opposite from needle assembly 15. Body 102 and plunger 104 are configured so that the practitioner can conveniently manipulate syringe 100 by placing his or her fingers on a finger rest (not shown) formed on body 102 and the thumb on a thumb rest (not shown) formed on plunger 104, thus allowing the practitioner to actuate plunger 104 with his or her thumb to force fluid into or out of the syringe body 102 in the conventional manner. Syringe body 102 comprises an internally threaded nose portion 102a that is dimensioned and configured to engage the threads 32 on hub 20 of the self-blunting needle assembly 15. Self-blunting needle assembly 15 is, accordingly, threaded into nose portion 102a of syringe body 102. Prior to using syringe 100, blunting member 14 is in the retracted position, as shown in FIG. 7. After syringe 100 is filled with the injection fluid, needle cannula 18 is inserted through the patient's skin. At this stage, detents 30 engage groove 30a, as shown in FIG. 3. Plunger 104 is then advanced to force the injection fluid through the central bore of blunting member 14 and out from needle cannula 18 into the patient's body. As plunger head 106 moves through the final stage of its stroke for full delivery of the fluid in syringe 100, it bears on blunting member assembly 15, specifically on end 14b thereof, and serves as an actuation member by forcing blunting member 14 to move from the retracted position (shown in FIGS. 3 and 7) to an extended position (shown in FIG. 4) in which the blunt end 14a of blunting member 14 extends beyond the puncture tip 18a of needle cannula 18. The blunting member assembly 15 is retained in the extended position by the function of detents 30 as they fall into groove 30b, as shown in FIG. 4.

Figure 8A:
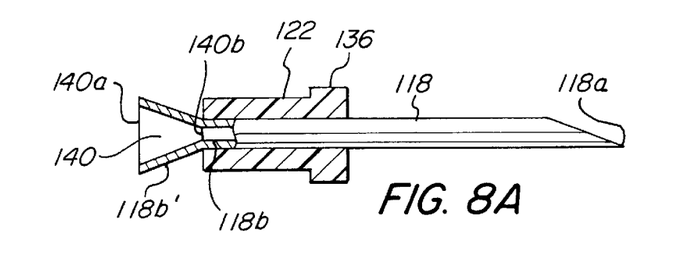
FIG. 8A is a side view in elevation, partly broken away, of another embodiment of the cannula member of the external component usable in a self-blunting needle device similar to that illustrated in FIG. 1.

FIG. 8A shows another embodiment of a needle cannula and the parts thereof identical or similar to those of the needle cannula illustrated in FIGS. 1–4 are identified by numbers which are 100 higher than those used in the FIGS. 1–4 embodiment. Thus, FIG. 8A shows a needle cannula 118 having a puncture tip 118a and a proximal end 118b. In this embodiment, proximal end 118b has a radially expanded, i.e., outwardly flared, extension 118b' to provide a first guide surface 140 which converges from a first entry aperture 140a to a first gate aperture 140b. In the illustrated embodiment, there is no need for a second guide surface analagous to second guide surface 42 of the FIGS. 1–4 embodiment, because the bore of needle cannula 118 is already coaxially aligned with first gate aperture 140b. In the illustrated embodiment, a mounting ferrule 122 has a circumferential ferrule flange 136 formed thereon for mounting needle cannula 118 in a manner similar or identical to the embodiment of the invention illustrated in FIGS. 1–4. Needle cannula 118 may be efficiently mounted within ferrule 122 by providing ferrule 122 as a split body which is fitted around needle cannula 118, in order to avoid the difficulty (solved by second guide surface 42 in the other illustrated embodiments) of properly coaxially aligning needle cannula 118 with the sleeve bore (unnumbered in FIG. 8A, but analagous to sleeve bore 38 of FIG. 1A) of mounting ferrule 122'.

Figure 8B:
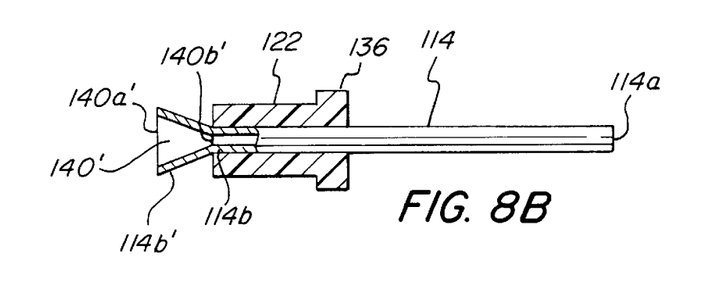
FIG. 8B is a view similar to FIG. 8A of another embodiment of the cannula member of an external component utilizable in a self-blunting needle device similar to that illustrated in FIG. 1.

FIG. 8B shows a blunting member of the type illustrated in FIGS. 5 and 6, wherein the external component is comprised of the blunting member. Accordingly, parts in FIGS. 8B identical or similar to those of FIGS. 5 and 6 are numbered at 100 higher than the corresponding components. Thus, FIG. 8B illustrates a blunting member 114 having a blunt end 114a and whose other end 114b has a radially expanded, i.e., outwardly flared extension 114b' to provide a first entry aperture 140a', a first gate aperture 140b' and a first guide surface 140. Blunting member 114 is, like needle cannula 118 of FIG. 8A, fitted with a mounting ferrule 122 having a circumferential ferrule flange 136 formed thereon.

While several preferred embodiments have been shown and described, various modifications and substitutions may be made thereto without departing from the spirit and scope of the invention. Accordingly, it is to be understood that the present invention has been described by way of illustration and not limitation.

What is claimed is:

1. A self-blunting needle cannula device comprising:
   (a) an external component comprising a needle cannula having an outside diameter, a through-bore having a through-bore diameter, a distal end comprising a puncture tip, a proximal end, and an external member hub on the needle cannula spaced from the distal end;
   (b) an internal component comprising an elongate blunting member having a distal end defining a blunt tip, and an internal component hub on the blunting member and spaced from the distal end, the blunting member being disposed within the through-bore of the needle cannula; wherein the external component and the internal component are movable relative to each other between a retracted position in which the blunt tip is positioned short of the puncture tip of the needle cannula to leave the puncture tip exposed, and an extended position in which the blunt tip extends beyond the puncture tip of the needle cannula to effectively blunt the puncture tip; and
   (c) a guide member at the proximal end of the needle cannula and having a first entry aperture of greater diameter than the through-bore inside diameter and a first gate aperture of lesser diameter than the first entry aperture, the first gate aperture being axially aligned with the through-bore adjacent to the proximal end of the needle cannula, the guide member defining a first guide surface that converges from the first entry aperture to the first gate aperture, to thereby guide insertion of the blunting member into the through-bore during assembly of the device; and wherein the guide member has a first end at which the first guide surface is formed and an opposite, second end at which is formed a second guide surface having a second entry aperture of greater diameter than the outside diameter of the needle cannula and a second gate aperture of lesser diameter than the second entry aperture, the guide member further comprising a sleeve bore extending between and axially aligned with the first and second gate apertures, the proximal end of the needle cannula being mounted within the sleeve bore and the needle cannula extending through the second gate aperture, and wherein the second guide surface converges from the second entry aperture to the second gate aperture, to thereby guide the proximal end of the needle cannula into the sleeve bore during assembly of the device.

2. The device of claim 1 further comprising a sealant lubricant disposed between the blunting member and the through-bore.

3. The device of claim 1 wherein the guide member comprises a ferrule disposed about the proximal end of the needle cannula.

4. The device of claim 3 wherein the ferrule is located within the external member hub.

5. The device of claim 1 wherein the guide member comprises a radially expanded extension of the proximal end of the needle cannula.

6. The device of claims 1 or 2 in combination with an actuation member for moving at least one of the blunting member and the needle cannula relative to each other to change the blunting member from its retracted position to its extended position.

7. A self-blunting needle cannula device comprising:
   (a) an external component comprising a needle cannula having an outside diameter, a through-bore having a through-bore diameter, a distal end comprising a puncture tip, a proximal end, and an external member hub on the needle cannula spaced from the distal end;
   (b) an internal component comprising an elongate blunting member having a distal end defining a blunt tip, and an internal component hub on the blunting member and spaced from the distal end, the blunting member being disposed within the through-bore of the needle cannula; wherein the external component and the internal component are movable relative to each other between a retracted position in which the blunt tip is positioned short of the puncture tip of the needle cannula to leave the puncture tip exposed, and an extended position in which the blunt tip extends beyond the puncture tip of the needle cannula to effectively blunt the puncture tip;
   (c) a guide member at the proximal end of the needle cannula and having a first entry aperture of greater diameter than the through-bore inside diameter and a first gate aperture of lesser diameter than the first entry aperture, the first gate aperture being axially aligned with the through-bore adjacent to the proximal end of the needle cannula, the guide member defining a first guide surface that converges from the first entry aperture to the first gate aperture, to thereby guide insertion of the blunting member into the through-bore during assembly of the device; and
   wherein the guide member is integrally formed as part of the external member hub.

8. A self-blunting needle cannula device comprising:
   (a) an external component comprising a needle cannula having an outside diameter, a through-bore having a through-bore diameter, a distal end comprising a puncture tip, a proximal end, and an external member hub on the needle cannula spaced from the distal end;
(b) an internal component comprising an elongate blunting member having a distal end defining a blunt tip, and an internal component hub on the blunting member and spaced from the distal end, the blunting member being disposed within the through-bore of the needle cannula; wherein the external component and the internal component are movable relative to each other between a retracted position in which the blunt tip is positioned short of the puncture tip of the needle cannula to leave the puncture tip exposed, and an extended position in which the blunt tip extends beyond the puncture tip of the needle cannula to effectively blunt the puncture tip;
(c) a guide member at the proximal end of the needle cannula and having a first entry aperture of greater diameter than the through-bore inside diameter and a first gate aperture of lesser diameter than the first entry aperture, the first gate aperture being axially aligned with the through-bore adjacent to the proximal end of the needle cannula, the guide member defining a first guide surface that converges from the first entry aperture to the first gate aperture, to thereby guide insertion of the blunting member into the through-bore during assembly of the device; and
wherein the guide member comprises a discrete ferrule which is mounted within the external member hub.

9. A self-blunting needle cannula device comprising:
(a) an external component comprising a needle cannula having an outside diameter, a through-bore having a through-bore diameter, a distal end comprising a puncture tip, a proximal end, and an external member hub on the needle cannula spaced from the distal end;
(b) an internal component comprising an elongate blunting member having a distal end defining a blunt tip, and an internal component hub on the blunting member and spaced from the distal end, the blunting member being disposed within the through-bore of the needle cannula; wherein the external component and the internal component are movable relative to each other between a retracted position in which the blunt tip is positioned short of the puncture tip of the needle cannula to leave the puncture tip exposed, and an extended position in which the blunt tip extends beyond the puncture tip of the needle cannula to effectively blunt the puncture tip;
(c) a guide member at the proximal end of the needle cannula and having a first entry aperture of greater diameter than the through-bore inside diameter and a first gate aperture of lesser diameter than the first entry aperture, the first gate aperture being axially aligned with the through-bore adjacent to the proximal end of the needle cannula, the guide member defining a first guide surface that converges from the first entry aperture to the first gate aperture, to thereby guide insertion of the blunting member into the through-bore during assembly of the device; and
wherein the diameter of the first gate aperture is less than the diameter of the sleeve bore to define a stop shoulder at the first gate aperture.

10. The device of claim 9 wherein the diameter of the first entry aperture is at least from about 2 to 10 times greater than the diameter of the sleeve bore.

11. The device of claim 9 wherein the diameter of the second gate aperture is substantially equal to the outside diameter of the needle cannula and the diameter of the second gate aperture is at least from about 2 to 10 times greater than that of the sleeve bore.

12. A method for assembling a self-blunting needle cannula device comprised of (i) an external component comprising a needle cannula having an outside diameter, a through-bore having a through-bore diameter, a distal end comprising a puncture tip, and a proximal end; and (ii) an internal component comprising an elongate blunting member having an outside diameter and a distal end, and, after assembly, being disposed within the through-bore of the needle cannula;

the method comprising the steps of:
(a) interposing between the external component and the internal component a guide member having a first end and an opposite, second end, the guide member having at its first end a first entry aperture of greater diameter than the outside diameter of the blunting member, and a first gate aperture of lesser diameter than the first entry aperture and open to the second end of the guide member, the guide member defining a first guide surface that converges from the first entry aperture to the first gate aperture;
(b) positioning the blunting member at the first end of the guide member with the blunt tip facing and in register with the first entry aperture;
(c) positioning the needle cannula at the second end of the guide member with the puncture tip in coaxial alignment with the first gate aperture; and
(d) advancing the blunting member and the first guide surface towards each other so that the blunt tip enters the first entry aperture and contacts the first guide surface, and continuing the advancing whereby the first guide surface guides the blunting member through the first entry gate thence into the through-bore of the cannula member.

13. The method of claim 12 wherein there is formed at the second end of the guide member a second entry aperture of greater diameter than the outside diameter of the needle cannula, a second gate aperture of lesser diameter than the second entry aperture, and a second guide surface which converges from the second entry aperture to the second gate aperture, the guide member further comprising a sleeve bore extending between and coaxially aligned with the first and second gate apertures,
wherein the positioning of step (c) further comprises disposing the needle cannula with its proximal end in register with the second guide surface and advancing the needle cannula and the second guide surface towards each other so that the puncture tip enters the second entry aperture and contacts the second guide surface and continuing the advancing whereby the second guide surface guides the proximal end of the needle cannula into the sleeve bore and seats the proximal end therein.

14. The method of claim 13 further comprising positioning the proximal end of the needle cannula within the sleeve bore immediately adjacent to the first entry gate.

15. The method of any one of claims 12 through 14 including leaving the needle cannula mounted within the guide member and utilizing the guide member as a component of the self-blunting needle cannula device.

16. The method of any one of claims 12 through 14
wherein the needle cannula and the blunting member are movable relative to each other between a retracted blunting member position in which the blunt tip is positioned short of the puncture tip of the needle cannula to leave the puncture tip exposed, and an extended blunting member position in which the blunt tip extends beyond the puncture tip of the needle cannula to effectively blunt the puncture tip;

the method further comprising the steps of installing the self-blunting needle assembly in a medical fluid handling device comprising an actuation member for moving the blunting member and the needle cannula relative to each other to change the blunting component from its retracted position to its extended position.

* * * * *